(12) United States Patent
Bower et al.

(10) Patent No.: US 8,026,101 B2
(45) Date of Patent: Sep. 27, 2011

(54) FAILURE DETECTION IN AUTOMATED CLINICAL ANALYZERS

(75) Inventors: Randy Kristopher Bower, Pittsford, NY (US); Stuart Gilmour MacDonald, Pultneyville, NY (US); James David Shaw, Hilton, NY (US); Mark Alan Simon, Pittsford, NY (US); Michael Avdenko, Rochester, NY (US); Joseph John Dambra, Rochester, NY (US); David Donald Hyde, Ontario, NY (US); Merrit Nyles Jacobs, Fairport, NY (US); James Daniel Riall, Roanoke, VA (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 1340 days.

(21) Appl. No.: 11/091,283

(22) Filed: Mar. 28, 2005

(65) Prior Publication Data
US 2005/0196867 A1 Sep. 8, 2005

Related U.S. Application Data

(62) Division of application No. 09/482,599, filed on Jan. 13, 2000, now abandoned.

(51) Int. Cl.
*B01L 3/02* (2006.01)
(52) U.S. Cl. ............. 436/43; 436/54; 436/180; 422/501
(58) Field of Classification Search .................... 436/49, 436/54, 180; 422/63–67, 100, 501
See application file for complete search history.

(56) References Cited

U.S. PATENT DOCUMENTS

| 3,232,429 | A | | 2/1966 | Norwich |
| 5,005,434 | A | | 4/1991 | Watanabe et al. |
| 5,315,529 | A | | 5/1994 | Farmer |
| 5,581,490 | A | | 12/1996 | Ferkinhoff et al. |
| 5,590,052 | A | | 12/1996 | Kopf-Sill et al. |
| 5,642,761 | A | * | 7/1997 | Holbrook ...................... 141/104 |
| 5,646,049 | A | | 7/1997 | Tayi |
| 5,710,723 | A | | 1/1998 | Hoth et al. |

(Continued)

FOREIGN PATENT DOCUMENTS

EP  0438159 A  7/1991

(Continued)

OTHER PUBLICATIONS

EPO Search Report, dated Aug. 25, 2003, for EPO Appln. No. EP 01 30 0244.

(Continued)

*Primary Examiner* — Jan Ludlow

(57) ABSTRACT

The invention is a method for detecting failures in an analyzer for conducting clinical assays. Potential errors that can result in assay failures in an analyzer are identified, as are their potential sources. The probability that an error source so identified will result in a clinically significant error is also determined. Available potential detection measures corresponding to the source of potential errors are identified with a combination of such measures selected and implemented based on their probability of detecting such errors within an acceptable limit with a concomitant low probability of the false detection of an assay failure. Each of the measures selected are functionally independent of others chosen to address the source of the error and are not subject to the same inherent means of failed detection. Applications of the method in a clinical analyzer are also presented.

9 Claims, 6 Drawing Sheets

U.S. PATENT DOCUMENTS

| | | | |
|---|---|---|---|
| 5,880,364 A | 3/1999 | Dam | |
| 5,885,530 A | 3/1999 | Babson et al. | |
| 5,987,399 A | 11/1999 | Wegerich | |
| 6,082,419 A * | 7/2000 | Skell et al. | 141/198 |
| 6,148,666 A * | 11/2000 | Roesicke | 73/290 R |

FOREIGN PATENT DOCUMENTS

| | | | |
|---|---|---|---|
| EP | 0506022 A | 9/1992 | |
| EP | 0527059 A | 2/1993 | |
| EP | 0732 598 A | 9/1996 | |
| EP | 0753 750 A | 1/1997 | |
| EP | 0866336 A | 9/1998 | |
| EP | 1 116 953 A2 | 7/2001 | |
| JP | 59-017161 | 1/1984 | |
| JP | 02-040562 | 2/1990 | |
| JP | 03-180764 | 8/1991 | |
| JP | 05-232125 | 9/1993 | |
| JP | 05-281106 | 10/1993 | |
| JP | 06-094730 | 4/1994 | |
| WO | WO 97/22007 A1 | 6/1997 | |
| WO | WO 9843052 A | 10/1998 | |
| WO | WO 9930170 A | 6/1999 | |

OTHER PUBLICATIONS

Korean Intellectual Property Office, Office Action Dated Dec. 7, 2006 (best available translation included).
Canadian Office Action Dated Jul. 23, 2007.
Canadian Office Action Dated Sep. 22, 2008.
Japanese Notice of Reasons for Rejection (Translation) Mailing Date May 11, 2010.
European Communication Mailing Date Dec. 10, 2010.

* cited by examiner

FAILURE DETECTION IN AUTOMATED CLINICAL ANALYZERS

CROSS REFERENCE TO RELATED APPLICATIONS

This application is a divisional application of U.S. Ser. No. 09/482,599, filed Jan. 13, 2000 now abandoned.

BACKGROUND OF THE INVENTION

The invention relates to analyzers for conducting a range of clinical assays.

Automated analyzers are a fixture in the clinical laboratory. Assays that used to require significant manual human involvement are now handled largely by loading samples into an analyzer, programming the analyzer to conduct the desired tests, and waiting for results. The range of analyzers and methodologies in use is large. Some examples include spectrophotometric absorbance assay such as end-point reaction analysis and rate of reaction analysis, turbidimetric assays, nephelometric assays, radiative energy attenuation assays (such as those described in U.S. Pat. Nos. 4,496,293 and 4,743,561 and incorporated herein by reference), ion capture assays, colorimetric assays, fluorometric assays, electrochemical detection systems, potentiometric detection systems, and immunoassays. Some or all of these techniques can be done with classic wet chemistries; ion-specific electrode analysis (ISE); thin film formatted "dry" chemistries; bead and tube formats or microtiter plates; and the use of magnetic particles. U.S. Pat. No. 5,885,530 provides a description useful for understanding the operation of a typical automated analyzer for conducting immunoassays in a bead and tube format and is incorporated herein by reference.

Despite the array of different analyzer types and assay methodologies, most analyzers share several common characteristics and design features. Obviously, some measurement is taken on a sample. This requires that the sample be placed in a form appropriate to the measurement technique. Thus, a sample manipulation system or mechanism is found in most analyzers. In wet chemistry devices, sample is generally placed in a sample vessel such as a cup or tube in the analyzer so that aliquots can be dispersed to reaction cuvettes or some other reaction vessel. A probe or proboscis using appropriate fluidics such as a pumps, valves, liquid transfer lines such as pipes and tubing, and driven by pressure or vacuum are often used to meter and transfer a predetermined quantity of sample from the sample vessel to the reaction vessel. The sample probe or proboscis or a different probe or proboscis is also often required to deliver diluent to the reaction vessel particularly where a relatively large amount of analyte is expected or found in the sample. A wash solution and process are generally needed to clean a nondisposable metering probe. Here too, fluidics are necessary to accurately meter and deliver wash solutions and diluents.

In addition to sample preparation and delivery, the action taken on the sample that manifests a measurement often requires dispensing a reagent, substrate, or other substance that combines with the sample to create some noticeable event such as florescence or absorbance of light. Several different substances are frequently combined with the sample to attain the detectable event. This is particularly the case with immunoassays since they often require multiple reagents and wash steps. Reagent manipulation systems or mechanisms accomplish this. Generally, these metering systems require a wash process to avoid carryover. Once, again, fluidics are generally a central feature in the conduct of these operations.

Other common systems elements include measurement modules that include some source of stimulation together with some mechanism for detecting the stimulation. These schemes include, for example, monochromatic light sources and calorimeters, reflectometers, polarimeters, and luminometers. Most modem automated analyzers also have sophisticated data processing systems to monitor analyzer operations and report out the data generated. Numerous subsystems such as reagent cooler systems, incubators, and sample and reagent conveyor systems are also frequently found within each of the major systems categories already described.

An assay failure, as the term is used in this specification, occurs when an assay result is obtained that is believable yet unacceptably inaccurate and if used as the sole source of clinical data would result in an improper clinical choice (i.e., treatment). Inaccuracies or a loss of precision can occur as a result of an almost endless list of factors such as mechanical noise or even inefficient programming protocols. Most of these are relatively easy to address. However, with analyte concentrations often measured in the µg/dL, ng/dL, or even MlU/L range, special attention must be paid to sample and reagent manipulation systems and those supporting systems and subsystems that affect the sample and reagent manipulation systems. The sample and reagent manipulation systems require the accurate and precise transport of small volumes of liquids and thus generally incorporate extraordinarily thin tubing and vessels such as those found in sample and reagent probes. Most instruments require the simultaneous and integrated operation of several unique fluid delivery systems, each one of which is dependent on numerous parts of the hardware/software system working correctly. Some parts of these hardware/software systems have failure modes that may occur at a low level of probability. A defect or clog in such a probe can result in wildly erratic and inaccurate results and thus be responsible for assay failures. Likewise, a defective washing protocol can lead to carryover errors that give false readings for a large number of assay results involving a large number of samples. This can be caused by adherence of dispensed fluid to the delivery vessel (e.g., probe or proboscis). Alternatively, where the vessel contacts reagent or diluent it can lead to over diluted and thus under reported results. Entrainment of air or other fluids to a dispensed fluid can cause the volume of the dispensed fluid to be below specification since a portion of the volume attributed to the dispensed fluid is actually the entrained fluid.

One method of ameliorating failures is through the detection of system errors. Once detected, unacceptable results can be appropriately dealt with or discarded and can prevent an improper clinical choice. The instrument can be made to provide an error message, discard unreliable results, cease further processing of a sample assay, perform an additional or confirmatory assay, or conduct further instrument diagnostics by virtue of mechanical/hardware systems or by software driven protocols for dealing with the errors. For example, liquid level sensors are frequently used to detect whether sample volume dispensed into a cuvette is sufficient to conduct an assay. The volume of cuvette contents is then incorporated into an algorithm within the system software. If it falls below a predetermined level, the algorithm instructs the instrument not to continue the assay and to generate a message indicating that the sample volume is insufficient to conduct the test requested for that sample.

Indeed, given enough effort, it is often possible to consider a range of possible detection schemes to attack targeted failure modes. Within a given set of possible detection schemes various degrees of robustness or probability of detecting the failure mode will be available. Setting the detection threshold high enough to catch all failures will likely catch many non-failures. This is a serious system reliability and cost concern. In an emergency room environment, failure to report a result promptly can put the patient at risk. Thus, a dilemma can arise in which failure modes can be determined as well as a range of possible detection schemes for each of the failure modes yet implementation of each detection mode is also unacceptable. Selecting the proper combination of failure detection modes to reduce failure rates to an acceptable level with a concomitant low level of risk that an acceptable result will not be discarded is thus a formidable challenge.

U.S. Pat. No. 5,646,049 describes a system of scheduling operations in an automated analyzer. Sources of carryover and contamination are analyzed and addressed by sequencing various steps (e.g., pipetting and wash steps) in the analysis scheme to minimize their impact. The software establishes a matrix to identify when carryover or contamination is likely, based upon preceding and succeeding pipetting steps scheduled by the scheduler software. The apparatus and method, based upon values from the matrix corresponding to the preceding and succeeding pipetting steps, causes the analytical system to respond with appropriate wash characteristics to eliminate the possibility of undesirable carryover or contamination when they appear likely. The matrix identifies whether or not a step is likely to introduce an error such as carryover. There is no quantification of the probability that such an error will occur and the probability that the error will have particular clinical significance or the extent of the error. In other words, potential error sources are addressed as individual events and not as having a compounding effect.

Under the FDA's Quality System Regulations for Medical Devices, developers of diagnostic equipment must go through a process to identify and rank potential system hazards, assess probability and severity, mitigate the high level hazards and quantify the new level of the mitigated risk. Hazard Analysis and Failure Modes and Effects Criticality Analysis are tool commonly used in the industry. Redesign of the system may be able to reduce the probability of a risk to a level where the possibility of occurrence is extremely remote. Often, it is necessary to add systems to detect the occurrence of the failure and prevent the reporting of the result associated with that occurrence.

The typical practice in the diagnostic industry is to design a detection system to detect a specific failure mode. Occasionally, the detection system may detect multiple failure modes, but that situation is more by good fortune rather than by intent. If the effect of a failure mode is an assay failure as defined earlier, the detection system must be tuned to a very high level of effectiveness. This tuning usually leads to serious difficulties.

Firstly, the detection system may cause potentially good results to be discarded. A population of the parameter being monitored, e.g. distance, volume, voltage, will likely exhibit a normal, Gaussian distribution with the aim point for the parameter, hopefully, at the center of the distribution. In a typical system, the parameter could vary around the set point by plus or minus 3 or 4 standard deviations without negatively effecting the final result. The detection system will also have some inherent measurement error or noise, such that repeated measurements of the same parameter will also form a normal distribution with the center of the distribution, hopefully, at the desired detection limit for the parameter. In almost all cases, the detection system must perform its function without effecting the parameter. For instance, volume measurements must take place without contaminating the fluid, temperature measurements must not alter the temperature of the object being monitored. Also, the detection system must work within timing and cost constraints of the instrument. The net effect of these limitations is that the measurement error may be significantly higher than may be desired. In other words, the normal curve represented by the detection system is wide. When the placement of the detection limit relative to the parameter set point causes the two normal distributions to overlap, the area under the intersection of the curves represents the cases where parameters that could yield valid results will be discarded by the detection system. The cost of achieving a high level of effectiveness for the detection system is a high number of discarded good results.

Secondly, the cumulative effect of multiple detection systems with respect to false positives, i.e. discarded good results, is additive. The more detection systems within a diagnostic instrument, the higher the number of false positives. If each significant failure mode had a separate detection system, the total number of detection systems would be high. In many cases, a detection system for a particular failure mode would require additional hardware. This adds more cost and further-degrades instrument reliability.

Thirdly, another consideration is the cost of developing highly effective detection systems. For example to verify that a detection system has achieved a effectiveness of 99.9% or better, a run of more than 4600 tests must be free of any of the errors being evaluated. Preferably, this test should be performed on multiple instruments. Verifying higher levels of effectiveness can become impractical in terms of time and cost.

It can be seen that it would be highly desirable to achieve high detection effectiveness by some other way than by attacking each failure mode individually.

The accuracy and precision of automated clinical analyzers can be improved by considering the cooperative effects of improvements in the sample and reagent manipulation systems and implementing those improvements in the components of those systems. Such an approach would also suggest new operations to reduce errors where the optimization of existing processes (e.g., probe wash steps) would not reduce the probability or extent of an error to the required degree. It would also suggest such new operations where the probability or extent of multiple errors could be better addressed by a nonexistent operation.

SUMMARY OF THE INVENTION

The invention is a method for detecting failures in an analyzer for conducting clinical assays. Potential errors that can result in assay failures in an analyzer are identified, as are their potential sources. The probability that an error source so identified will result in a clinically significant error is also determined. Available potential detection measures corresponding to the source of potential errors are identified with a combination of such measures selected and implemented based on their probability of detecting such errors within an acceptable limit with a concomitant low probability of the false detection of an assay failure. Each of the measures selected are functionally independent of others chosen to address the source of the error and are not subject to the same inherent means of failed detection.

Another aspect of the invention is a method of detecting fluid metering failures. In this method a fluid delivery device that dispenses fluids is rapidly flushed with a fluid in a vessel so that a short-lived foam is formed by the flushed liquid. The height of the foam within the vessel is sensed and used to determine the volume of liquid dispensed. The volume of the dispensed liquid is then evaluated to determine its sufficiency.

Insufficient volumes are recorded as fluid metering failures. Preferably, the fluid delivery device is a probe or proboscis.

Another aspect of the invention is a method of detecting failures in assays that require sample dilution. In this method, sample is aspirated in a fluid delivery device and then metered into a dilution vessel such as a cup (alternatively, referred to a well throughout). Diluent is metered into the dilution vessel. Reagent can then also be metered into the dilution vessel. The volume of either the sample plus diluent or the volume of sample plus reagent plus diluent is determined. If any such volume is insufficient for conducting an assay, it is identified as a failure.

Another aspect of the invention is a carryover free fluid delivery and verification device. The device is a hollow vessel through which fluid can be aspirated. The end of the vessel is noncircular in its cross section and is in contact with a transducer. The end of the vessel has a geometry and dimensions that are resistant to carryover. It is made of a material that allows contact with dispensed fluid to be communicated via the transducer to a level determining device. Preferably, the end of the vessel is a notched tooth and the device is a probe or proboscis.

In yet another aspect of the invention, a carryover free fluid deliver and verification device is used to assess fluid level in a vessel and can aspirate fluid from the vessel as necessary as well as verify sample and reagent volume, wash volume, wash fluid residual level, and signal reagent volume.

DETAILED DESCRIPTION OF THE INVENTION

The invention involves methods and devices for detecting failures in an analyzer for conducting clinical assays. Multiple detection schemes are identified for the detection of the same failure mode. In this was, for a failure mode to be undetected, it would have to pass through several, serial detection schemes, each with its own probability of detection. The probability of that failure mode to pass through any combination of the detection schemes undetected would be 1 divided by the product of the detection probabilities for each affected scheme. By taking advantage of the multiplying effect of multiple detection schemes targeting the same failure mode, each detection scheme does not have to be extremely robust in order to achieve a robust detection system. At the same time, a combination of detection schemes can be selected so that properly conducted functions are not erroneously determined to be failures.

As a general matter, the analyzer is first conceptually categorized into systems of components and, where appropriate, those systems are categorized further into subsystems. The systems and subsystems are logical categories that operate together to perform a discrete function. These can include, for example, sample and reagent manipulation systems as described above, measurement systems that can further be comprised of systems for stimulating reagent-sample combinations and reading the signal generated in the process (e.g., a luminometer), data processing systems that may include quality control systems or subsytems (e.g., statistical analysis and reporting algorithms and databases), reagent treatment and storage systems, reaction preparation and treatment systems such as incubators, robotics control systems, communication systems that include components such as modems, internal diagnostics systems within or separate from the aforementioned systems, disposable preparation and treatment systems for the production and disposable of various disposals such as cuvettes and cups, and other auxiliary systems such as wash fluid delivery systems.

Figure 1:
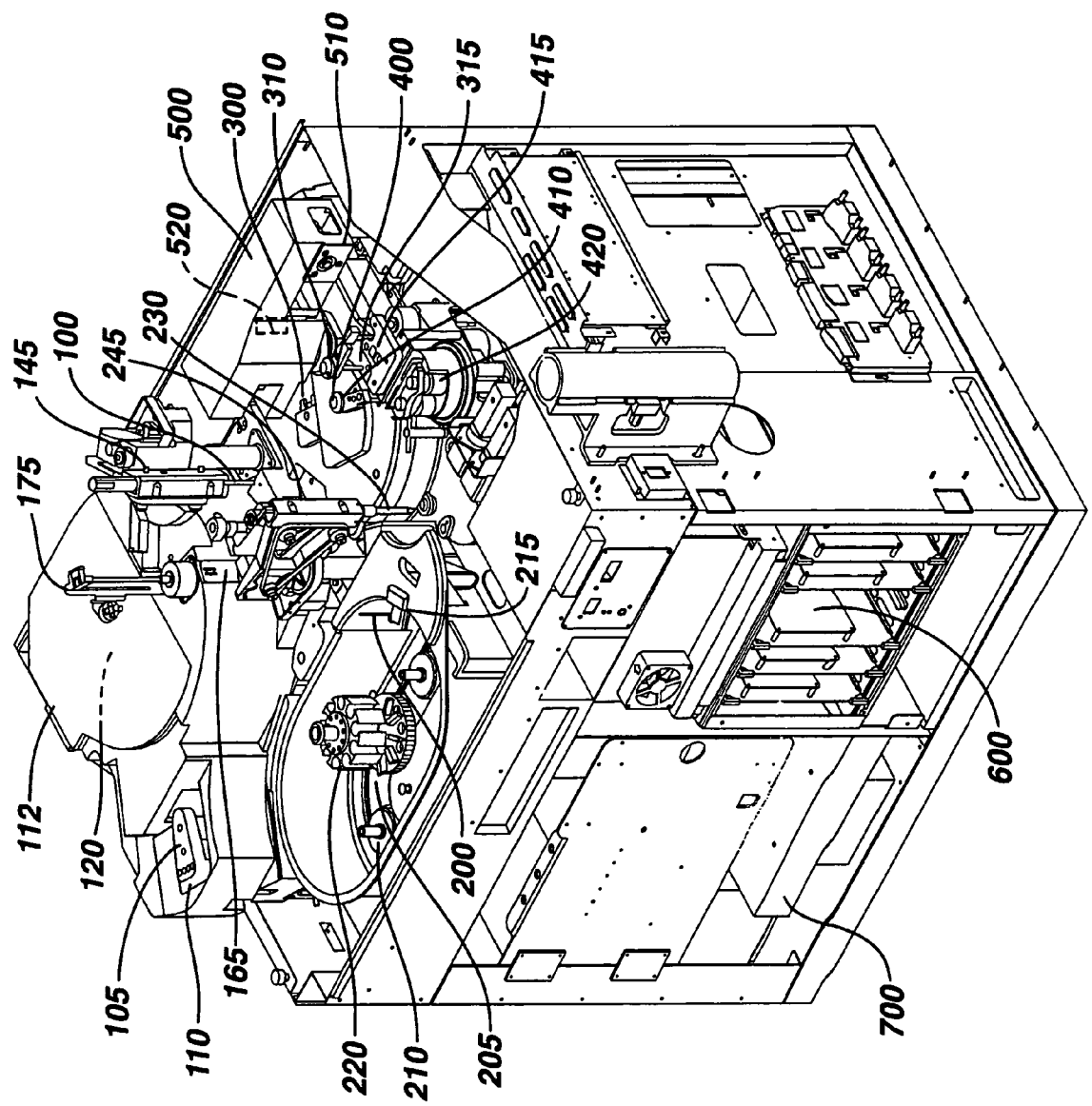
FIG. 1 is an isometric view of a clinical analyzer.

FIG. 1 shows components of the preferred clinical analyzer addressed in this specification. This analyzer is designed to conduct automated enzyme immunoassays (EIAs) for analytes including hormones, vitamins and related compounds, infectious disease markers, cancer markers, therapeutic drug monitoring, abused drug analysis, and other analytes amenable to analysis by EIA. To help further understand the invention, the operation of the systems is broadly described with respect to the way an assay would be conducted on a sample. Of course, the described analyzer is only exemplary and the methods described and claimed in this specification have general applicability in the field of clinical analyzers.

Figure 2:
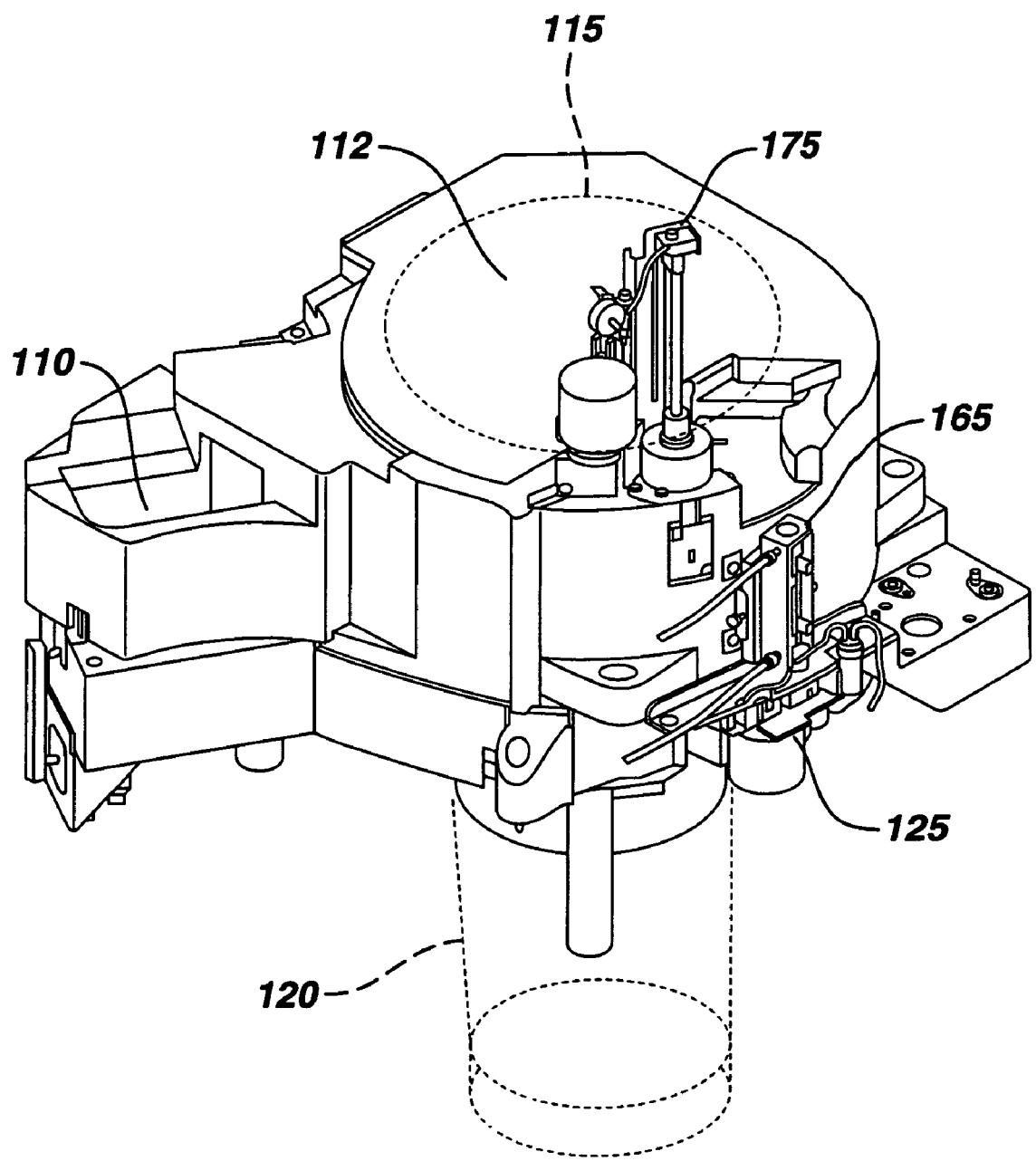
FIG. 2 is an isometric view of a portion of the reagent management system of a clinical analyzer.

FIG. 1 shows the relationship of the reagent management system to the other systems of the analyzer while FIG. 2 shows portions of this system in more detail. Throughout this specification, reference numbers are applicable to any figure in which such components are shown.

Figure 2A:
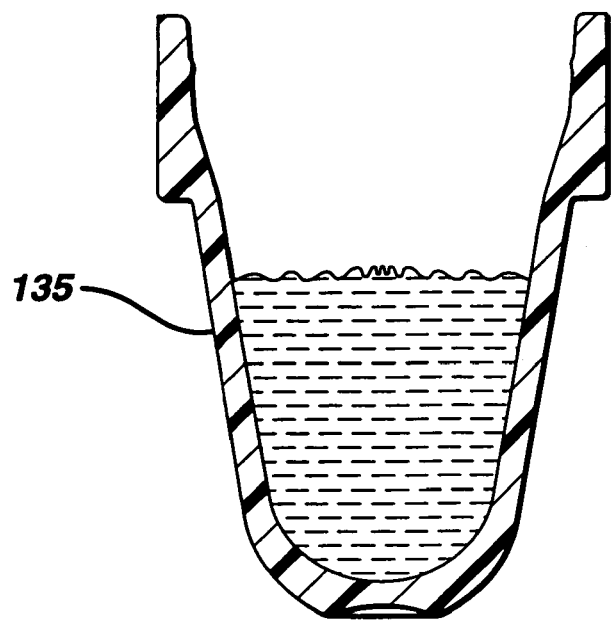
FIG. 2A is a cross-sectional side view of a well containing a reagent or sample fluid.

The reagent management system conducts reagent scanning for input into the data processing mechanism of the analyzer and meters and dispenses reagent to the reaction vessels (such as wells 135 shown in FIG. 2A and described below) via reagent probe 100. Reagent packs 105 are external to the system but are components that are manipulated by the reagent management system; they are configured to contain the reagents necessary to conduct an immunoassay. Typically, they include one or more antigenic or antisera components used to combine with the analyte and provide adhesion to or with a reaction vessel. Preferably, reagent packs 105 are configured with a spring-loaded supply of reaction vessels such as reaction wells of an appropriate volume and geometry for the assay. Preferably, 0.35 ml, conical wells coated with a material complementary to the reagents are used as reaction wells. Well coatings can comprise materials such as streptavidin and/or other materials useful for immunochemical analysis as is well known in the art to facilitate binding by a biotinylated antigen or antibody to which an analyte binds as part of the assay chemistry.

Figure 4:
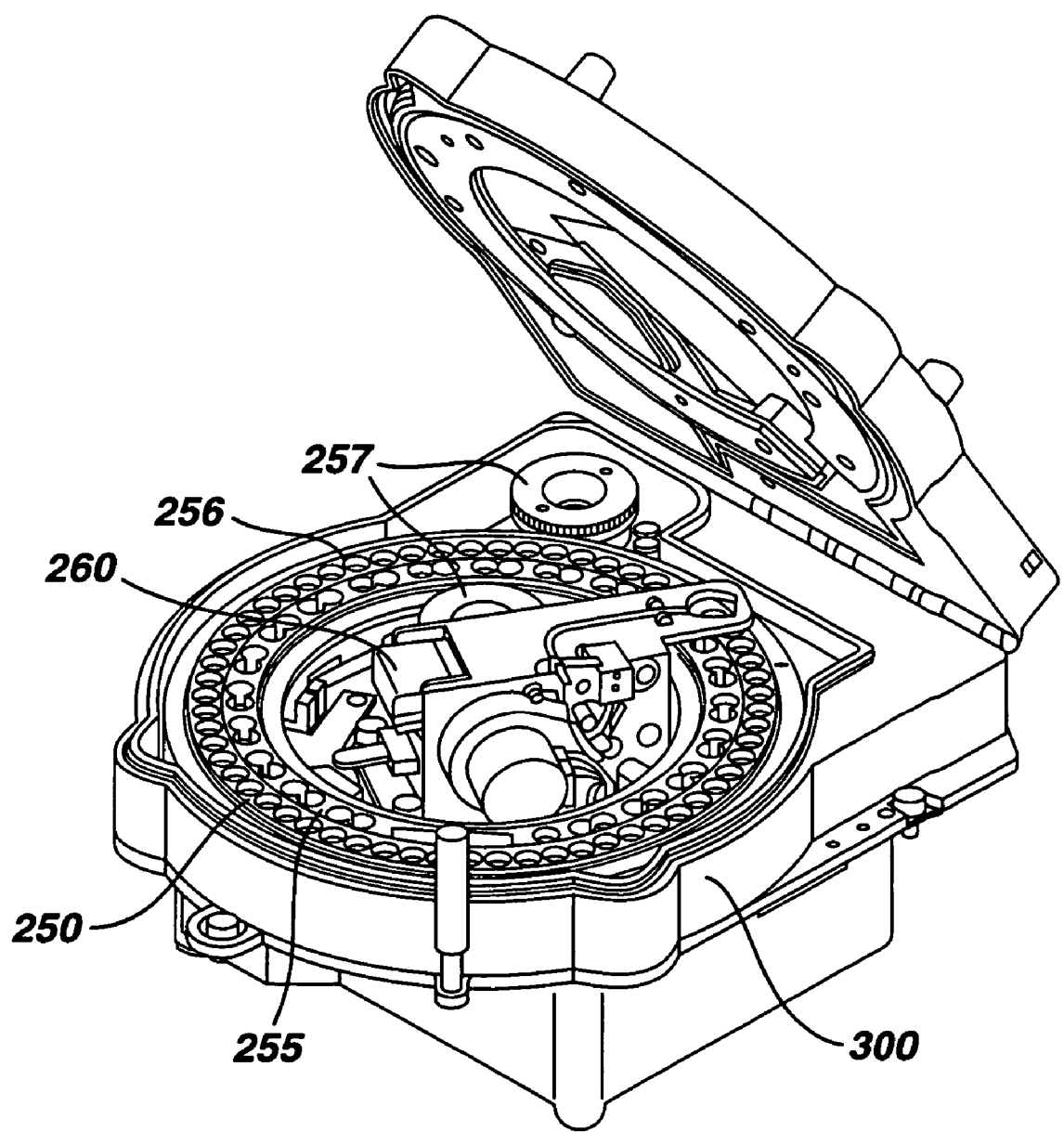
FIG. 4 is an isometric view of an incubator and various other subsystems of a processing system of a clinical analyzer.

The reagent management system is comprised of a number of subsystems and components. Autoload station 110 shuttles reagent packs to the reagent supply substation 112 by any suitable drive mechanism such as a chain and sprocket, belt and pulley, gear train, linked belt mechanism, a driven series of mechanical links such as pawl links, or the like. Preferably, a system of epicyclic gears is used in which a geared ring is fitted with a slotted overlay corresponding to the shape of the reagent pack. The reagent pack is then inserted into a slot along the movable portion of the substation and is driven in a circular motion by a pinion on the interior of the ring (shown schematically in phantom in FIG. 2). In this way, the reagent packs can be stored for access and rotated to an appropriate position for aspiration and dispensing by the reagent management system. The reagent management system is further comprised of a reagent supply cooler 120 that cools the interior of the reagent supply substation according to the functional requirements of the reagents (typically, 3-15° C., preferably 4-10° C.). In this way, reagent supply cooler 120 maintains reagents and reaction vessels at the appropriate humidity and temperature. The reagent well shuttle 125 extracts wells and deposits them in outer ring 250 of the processing system (see FIG. 4). The wells 135 are extracted from their storage area (preferably, in the reagent packs) by an extraction device (not shown) comprising a portion of well dispenser 175 that functions in concert with the reagent well shuttle 125. This can comprise any convenient mechanism such as hydraulic plunger having a prong at one end corresponding to the shape of the well. The mechanism is preferably pivotable so that once grabbed, a well can be moved to a portion of the instrument wherein it will be filled with sample and/or reagent.

The reagent metering subsystem is comprised of a reagent metering arm 145 having a reagent probe 100 movably attached to it. Reagent metering arm 145 is pivotable so that it can position the reagent probe 100 in position to dispense reagent or diluent into a reaction vessel. Reagent probe 100 aspirates, transports, and dispenses reagent and/or diluent into reaction vessel. It is generally configured so that it also moves in a vertical direction to dip into reagents and lower itself into the vicinity of the reaction vessel (well). This is accomplished by any of the well known mechanisms for affecting vertical motion such as gear train with step motor, belt and pulley assembly, pneumatic or hydraulic lifts, or the like. A stepper motor with fine steps (at least about 390 steps per cm of vertical motion are desired) connected to a rack and pinion drive is the preferred mechanism for regulating vertical motion. Where pivoting is required, a stepper motor with fine steps is also preferred (generally, at least about 1720 steps per revolution of the shaft used to rotate the probe or probe arm are desired) with the pinion comprising or attached to the outer diameter of the shaft that is rotated. Control of stepper motors, and hence probe and mechanism movement, is accomplished by techniques well known in the art such as those described in U.S. Pat. No. 5,646,049 which is incorporated herein by reference.

Figure 2B:
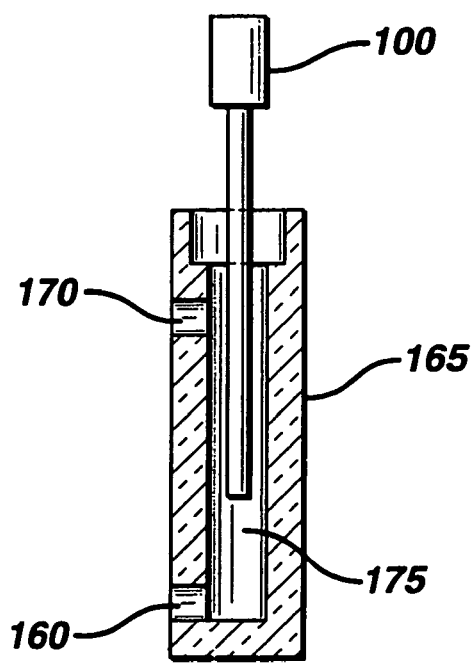
FIG. 2B is a cross-sectional side view of a reagent probe wash station.

In operation, the reagent probe 100 aspirates and dispenses fluids via connection to a fluidics systems comprised of valves, pumps, tubing, and the like. It is preferably charged by vacuum and can disperse by release of vacuum or by pressurization. Whenever reagent metering involves aspirating and dispensing different reagents, it is desirable to include a wash step so that the reagent metering probe does not carry over reagent from one step of an assay into a different step of the assay or into a different assay. This helps avoid small inaccuracies. The wash step involves flushing the probe with a wash fluid after delivery of each reagent component. Thus, the reagent probe 100 is also connected via fluidics systems to a wash solution. The probe 100 can be charged and dispense wash fluid by vacuum or by pressure. As shown in FIG. 2B, reagent probe wash station 165 provides an enclosed space for the probe 100 to conduct the wash step. In operation, the probe is lowered into the wash cylinder 175 of the wash station, wash fluid is charged through the probe and into the wash cylinder 175 and evacuated through the outlet port, 160. Wash fluid is also charged through inlet port 170 to wash the exterior of the probe. Improvements to the wash operation and its new use in reagent metering verification are described further below.

Figure 3:
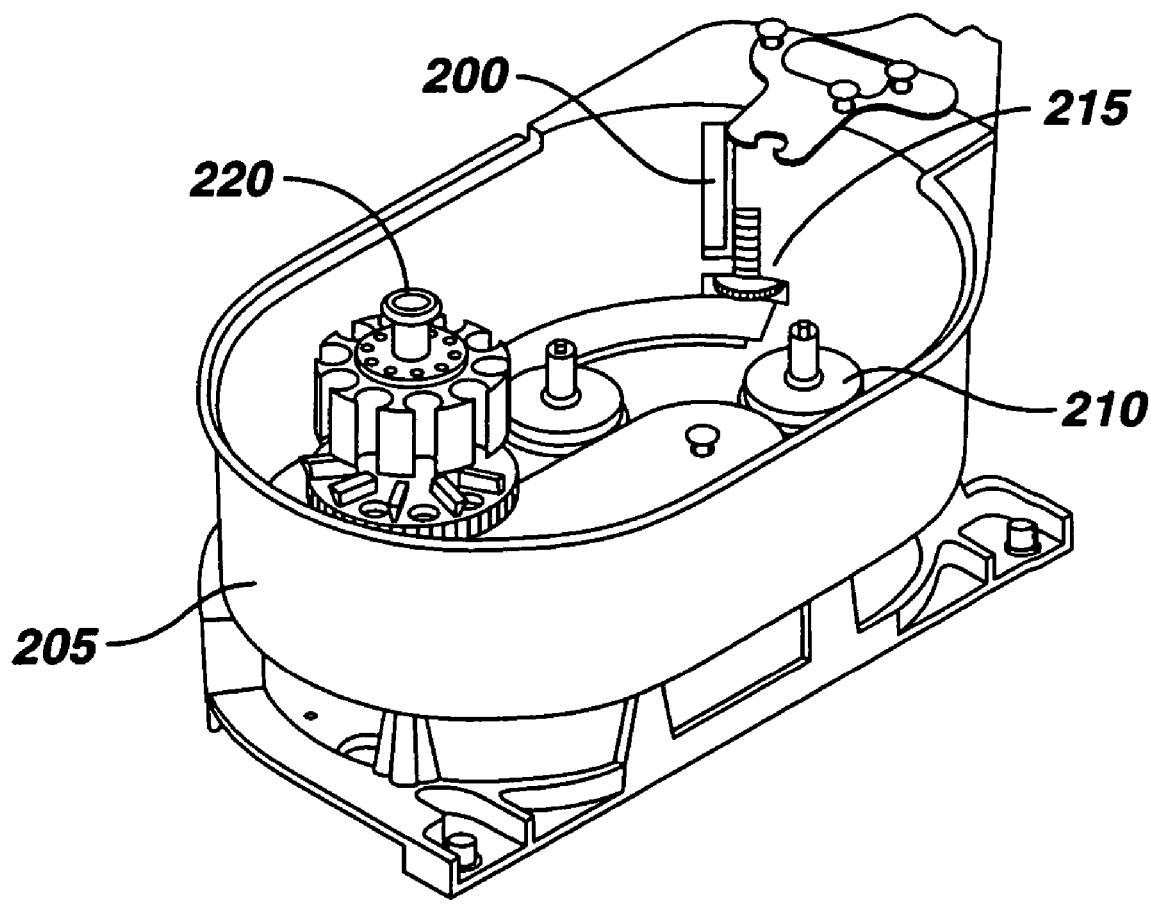
FIG. 3 is an isometric view of a sample management system of a clinical analyzer.

FIG. 3 and FIG. 1 are next considered together to describe the sample manipulation system that loads and meters sample to the appropriate reaction vessels (preferably, wells 135). It is also capable of providing input to the data processing systems via bar code reader 200 that reads bar codes that may be placed on patient sample vessels such as test tubes and the like. The sample manipulation system is also comprised of a number of subsystems and components. The sample supply subsystem is one which is comprised of a bar code reader 200 for inputting sample identification data as described above and a sample tray conveyor 205, one or more sample tray transports 210, and positioner 215 for moving sample to the sample metering station adjacent to the sample positioner (i.e. the position into which proboscis 230 is lowered, as described below).

The sample tray conveyor 205 can be any conveyor system for moving vessels and can employ an electrically or mechanically movable magnetic drive that propels a carousel 220 atop a sample tray transport 210 having a magnetic or ferrous component attractive to the magnetic drive. Alternatively, the sample tray conveyor 205 can comprise a motor driven chain and sprocket mechanism, a driven series of mechanical links such as pawl links, a belt driven system or the like. The preferred sample tray conveyor is an elliptical magnetically driven tracked system In this system, the sample tray is preferably a carousel 220 that sits atop a transport 210 that has a piece susceptible to magnetic attraction. This enables it to be moved around the ellipse through the rotation of a magnetic field around the perimeter of the elliptical track from a position beneath the sample trays. In this configuration, the outer diameter of the sample tray can be geared so that the tray can be rotated about its own central axis by a geared piece such as positioner 215 adjacent to the bar code reader 200 (or at any other convenient location around the exterior of the elliptical track).

The sample metering subsystem aspirates samples and dispenses them into reaction vessels via proboscis 230. The proboscis and its related metering arm 245 are preferably similar in design to the reagent metering arm 145 described above. Disposable tips (not shown) through which sample can be aspirated and dispensed are preferably fitted on the proboscis and are disposed after each aspiration and delivery of sample. The tips are preferably conical with the apex of the cone pointed toward down. Appropriate robotic commands are used to position the proboscis over the tips and then temporarily attach the tips via force (injection of the proboscis into the hollow portion of the tip). For convenience, a supply of tips can be maintained on a tip supply carousel (not shown). The tips can likewise be removed by raising the proboscis drive to its top most travel, activating an ejector sleeve (not shown). Generally, disposable tips are comprised of a molded thermoplastic such as polyethylene or polypropylene. Such tips avoid direct and repeated contact of sample and a singular proboscis end.

In operation, the sample metering subsystem functions similarly to that of the reagent metering system. Sample, loaded on sample carousel 220 is driven to a location reachable by the proboscis 230. After having loaded a disposable tip onto the proboscis, the system pivots the proboscis directly overhead a sample vessel. The proboscis is then lowered into a vessel such as a tube on the carousel where it aspirates a quantity of sample sufficient for the assay to be conducted. The proboscis is then pivoted to a position that is overhead a well residing in outer ring 250 (FIG. 4) where the sample is dispensed. It is preferable that the sample is dispensed into the well before reagent has been dispensed into the well. The proboscis can then be used to validate the proper metering of the sample into the well. This is accomplished by fitting the proboscis with a sensor such as an optical sensor on sample metering arm 245. The sensor (not shown) is in communication with a transducer (not shown) and the data processing system 600. The sensor preferably detects the level of the sample by pressure differential, through capacitance, or reflected energy as is known in the art. An optical sensor can also be used to home the proboscis to its proper position. After metering and measuring the sample, reagent is preferably dispensed into the well as described above. Mixing of sample and reagent is accomplished by dispensing reagent into the well containing sample with sufficient velocity to give partial mixing. Further mixing is accomplished by moving the incubator rings 250 and 255 at rapidly changing velocities.

Some assays require dilution of the sample. When this is the case, sample is first metered into a dilution vessel that is preferably substantially similar to the wells previously described except that they are not generally treated with any reagent or other materials to which added reagent will adhere. That is, they are functionally inert within the context of the immunochemical reactions of interest. Proboscis 230 is used to meter the sample as in other assays. Dilution wells are placed in outer ring 250 during the dilution operation. The reagent probe 100 meters and dispenses diluent into the dilution well. Preferably, diluent is added to the dilution well after the addition of sample but it is possible to add it before or after any component. It is also possible though less desirable to configure assays so that reagent is added before addition of sample or before addition of diluent. After diluent is added, the diluent and sample are mixed by aspiration of reagent and sample in the proboscis 230 and dispensing the combined fluid back into the well 135. This process of mixing by aspiration and dispensing is referred to as "swish mixing". Modifications to certain aspects of swish mixing for use in failure detection are described further below. Upon completion of mixing, proboscis 230 aspirates the diluted sample and dispenses it to a reaction vessel (well) on outer ring 250 for completion of the assay.

In the processing system, reaction wells containing sample, reagent, and (optionally) diluent are mixed with signal reagent, incubated. Chemiluminscence or other appropriate signal generation of the reaction of sample analyte and reagent(s) is also read in this system. Well wash arm 310 and well wash probe 315 are the principle components of the well wash subsystem whose function is to wash the wells and remove sample and unbound reagent (analyte is bound to the reaction vessel along with reagents that manifest the signal that is read later). Rings 250 and 255 reside within incubator 300. The rings are preferably of independent concentric epicentrically geared rings similar to that described for the autoload station 110. Such a configuration can be driven by pinions 257. Recesses 256 are conveniently placed along the curvature of the ring into which reaction and dilution wells can be placed. The temperature and humidity are controlled within incubator 300 for a time and at a temperature appropriate to the assays being performed. Incubation time can differ from assay to assay and is under the control of the data processing system.

Returning to the well wash subsystem, after appropriate incubation, well wash probe 315 (which is preferably similar in design to the reagent probe 100) is manipulated so that it aspirates and dispenses sample and unbound reagent out of the reaction wells and then dispenses wash fluid into the wells, aspirates and dispenses again. Thus, to this point within the reaction wells, reagent and analyte have reacted and have been adhered to the well. The well wash arm has removed materials that have not reacted and/or could otherwise. interfere with sample reading.

It is also possible to configure such an instrument so that the unmeasured materials would adhere to a reaction vessel and the contents of the vessel would be further processed or be subject to some reading. In such a case they would then have to be aspirated and dispensed to another vessel.

Upon completion of well washing, the well wash arm 310 articulates movably attached well wash probe 315 to a position to aspirate sample and unbound reagent and dispense wash fluid to the reaction vessel. Generally, wash fluid is dispensed as the well wash probe 315 is lifted out of the reaction vessel. The signal reagent subsystem comprises signal reagent arm 410, signal reagent probe 400, signal reagent (packs) 420, and prime/pump assembly 415 as its major components. Signal reagent probe 400 (which is preferably similar in design to the other probes already described), movably attached to signal reagent arm 410 aspirates, transport, and dispenses signal reagent from signal reagent pack 420 to the wells. Signal reagent arm 410 is fitted to a prime, pump assembly 415 for this purpose. Signal reagent is a composition that contains a component that produces a signal upon combination with the reacted reagent/sample combination (e.g., luminol derivatives). Luminometer 500 is comprised of a fiber optic bundle 510 that communicates with photomultiplier 520 which is in further communication with data processing system 600. In operation, the fiber optic bundle 510 is positioned over the sample with mixed reagent and, optionally, diluent. Chemilluminescent signals generated by the reacting reagent/sample combination are then transmitted to the photomultiplier that converts the light signal to an electrical signal for processing according to conventional digital techniques. An internal reference (not shown) can be used for calibration of the luminometer 500.

Data processing system 600 is an integrated array of circuitry used to coordinate the function of the systems and subsystems, conduct system diagnostics, calibrate instrumentation, record results, and analyze results. It includes well known processing devices such as microprocessors and may be in electronic communication with any number of external processing systems. For example, it may be linked through a local area network to other analytical instrumentation so that tests are scheduled and results are compiled and reported for a number of different assays, some of which are not conducted on the instrument described here.

A number of other systems are ancillary to the primary functioning of the instrument of this invention. These include, a supply center 700 for storage and dispensing of wash fluids. These fluids can be stored in a large container maintained under pressure by a pump. Appropriate fluidics such as tubes, pumps, and valves are used to drive the fluid to a working bottle that can be used to mix the fluid with other fluids prior to injection to one of the systems such as the reagent management system. Here too, the fluids can be driven via appropriate fluidics using pumps generating a positive force or vacuum. A filter such as a micropore filter is generally placed in one or more of the fluidics line prior to a point in which a fluid will be dispensed so that it is degassed enroute to the appropriate dispenser. This occurs as a result of the pressure gradient across the filter and leads to improved accuracy and precision in metering the fluid.

To summarize then, an assay is conducted as follows. Reagent packs containing reagents specific to the assays to be performed are loaded into auto-load station 110. The reagent packs are then shuttled into reagent supply substation 112 within the reagent supply carousel. Sample tubes are loaded onto sample carousel 220 which is placed in the sample conveyor. The sample conveyor 205 which moves the sample carousel to the positioner 215 which rotates the sample tray so that barcode reader 200 can input data about the identity of each sample tube into the data processing system 600 for assignment of tests and in preparation of result reports. Sample metering arm 245 moves proboscis 230 to a location above sample tubes. Proboscis 230 (with attached tips) is then lowered into the tube and aspirates 10-80 µl of sample. A reagent pack corresponding to an assay to be performed on the aspirated sample is then moved beneath the well dispenser 175 where a well is pushed into well shuttle 125 and then into the outer ring 250 within incubator 300. Outer ring 250 is then rotated to a position beneath proboscis 230. The sample metering probe or proboscis 230 is then rotated to an appropriate position above the well and dispenses between 10-80 µl of sample into the well corresponding to the assay to be performed. Reagent metering probe 100 which has been moved into an appropriate position by reagent metering arm 145 is in a position atop the reagent pack. Between 20 and 160 µl of reagent(s) are then aspirated. Outer ring 250 is then rotated to a position beneath reagent metering probe 100. The reagent metering probe 100 is then rotated to an appropriate position above the well and dispenses aspirated reagent into the well corresponding to the assay to be performed. The well is then rotated in the outer ring 250 within the incubator 300 for a time that is dependent on the assay to be conducted and is then moved to a position on the inner ring 255 by shuttle 260. The well wash probe 310 dispenses wash solution, aspirates unbound reagent and wash solution, and evacuates the Solution via system fluidics. Inner ring 255 is rotated so that the washed well is in a position in which signal reagent can be dispensed into the well via signal reagent probe 315. Signal reagent arm 410 moves signal reagent probe in position above signal reagent which is then aspirated. The probe is then moved to a position atop the well where it is dispensed. The well is then incubated for 5 minutes and rotated to a position where it is accessible to the luminometer 500 which reads one or more chemiluminescent emissions, converts the signal to an electrical one via photomultiplier 520 and, passes the readings to data processing system 600. The data processing system then uses the signal to attain and communicate a clinical result. The well is then disposed.

Once an analyzer is conceptually categorized according to systems and subsystems, potential sources of error are identified within each. That is, problems that do or can arise are linked to actual or possible error sources within the systems. For example, a failure could occur if an ineffectual quantity of reagent is used in the assay. Possible causes of such an event include, for example, an occluded reagent probe, clogged fluidic components, failure to detect empty or near empty reagent packs, false level sensing of fluid due to bubble formation on the top of the fluid, incorrect alignment of dispense systems during aspiration or dispensing.

The effect of each such cause is then quantified so that the extent of the contribution to a failure is associated with each possible cause. For example, a completely occluded reagent probe would result in a complete failure while a leaky pump would only affect the accurate dispensing of reagent by 0-50%. Likewise, the probability of each possible cause is quantified. This is done by evaluating usage data or by reiterative testing of the function of the component identified as a possible cause. For example, one can determine the statistically relevant number of occurrences of reagent aspiration that would be needed to determine the frequency of reagent probe occlusion and then actually conduct that number of operations to arrive at a measure of the probability of such an event.

Having determined the probability of possible failure causes, the chain of causal events is linked. That is, the failure causes associated with a particular failure are related to each other. Acceptable failure rates are then analyzed by conceptually selecting a combination of failure causes and multiplying the inverse of their probabilities to determine the reduction in the probability of the failure that would result from eliminating the causes of failure considered. Further, the effect of a possible false positive are considered for each iteration of failure analysis conducted in this manner. That is, the probability that an event will be construed to be a failure when it is not is also determined. For the most part, false positive conditions occur where the detection system makes an error in measurement or detection. For example, where a capacitance based detection method is used to detect the presence of a liquid subsequent to a step in which no liquid was present, the sensor will record an absence of liquid even where it is present when there is no transition in capacitance in the two steps. This can happen when the sensor is in contact with liquid even though the liquid was not dispensed such as could occur with a leaky component that continuously leaks fluid onto the sensor. In such a case, a failure to dispense liquid will have been signaled when such was not the case. The sensor remaining in contact with a wetted surface fools the sensor since no transition from wet to dry occurs when it enters the liquid that it is intending to sense. Thus, the method of the instant invention maximizes failure detection within the acceptable limits of attaining a false positive indication of a failure.

The probability of detecting the insignificant event is determined in the same manner as is the probability of the failure cause occurring. A combination of causes are targeted for detection such that their combined probabilities for detecting a failure would exceed the acceptable failure level and their probabilities of not detecting an insignificant event as a failure would be acceptable. A reasonably acceptable failure rate is 1 in 1,000,000 (i.e., the failure to detect a system failure 1 out of every 1,000,000 times such a failure occurs.)

The method is further illustrated by the following example. In detecting failures in the reagent metering operation a volumetric verification that checks fluidics can be performed on start-up that has an error probability of about 1 in 100. By adding another failure detection scheme during a wash step that verifies that the reagent probe has not been clogged another reduction of 1 in 100 probability of failing to detect a reagent metering problem is attained. Further, another 1 in 100 probability of failing to detect such a failure is attained by measuring the volume of a well once reagents and sample have been dispensed in it. This multi-level approach makes it possible to have detection processes that have an overall false negative frequency of less than 1 in 1,000,000 (i.e., $100^3$). If however, one or more of the proposed detection schemes would introduce a higher rate of false positives (i.e., it would be too sensitive) relative to other possible detection schemes, then one would employ the combination of schemes that would give the acceptable false negative rate with the lower false positive rate. This process permits a high rate of confidence in detecting failures without having to employ every possible means of failure detection.

The process can be quantified using statistical principles. For example, acceptable confidence intervals can be defined in terms of standard deviation computations. This can be used to determine whether and which proposed failure detection methods should be selected for implementation based upon whether the probability of detecting an error will fall within the desired confidence interval for both detection and false positives.

The foregoing process can also be modeled and is reducible to automation. For example, a linear program can be established for to optimize such a system using the Simplex method of linear programming. These methods are described in numerous well known references such as the following which are incorporated herein by reference. J. F. Shapiro, *Mathematical Progamming: Structures and Algorithms*, Wiley, 1979; D. G. Luenberger, *Introduction to Linear and Nonlinear Programming*, Addison-Wesley, 1973. The method involves minimizing a linear objective function of continuous real variables subject to linear constraints. In this case, false negatives could be defined as missed test failures and false positives as unnecessary lost tests. One would then optimize [1−C1(false negatives of a first defined type)+C2(false negative of a second defined type)+C3(false negative of a third defined type)+ . . . +Cn(false negative of n defined types)] (weighted benefit) against [A(false positive a first defined type+false positive of a second defined type+false positive of a third defined type.+fp#n)+B(UMC)+D(Dev$)] (weighted cost). The constants can be chosen to assign bias to the tests/systems as desired.

Commercial software can then be used to solve problems of this nature. Such programs include, for example, the AIMMS programs available from Paragon Decision Technology, GAMS programs available from the GAMS Development Corporation, and PREMIUM SOLVER programs available from Frontline Systems, Inc. These, programs can run on conventional computers including commercially available PCs, workstations, and mainframes. Computer programs for conducting such operations are also readily written in any convenient code such as C++ or VISUAL BASIC and can be stored on any convenient medium such as magnetic and optical storage medium including floppy disks and CDs.

The method of this invention will now be described with respect to its implementation in preferred embodiments. These embodiments concern failures that manifest themselves as an absence of a chemilluminescent signal or a signal that indicates less of an analyte than is actually present. Consideration of the causes of these failures identified three principle systems that could be at fault. First, the reagent management could produce such a failure by metering an improper quantity of reagent. Second, the signal reagent system could produce such a failure by metering an improper quantity of signal reagent. Thirdly, where assays require a dilution, the sample metering subsystem of the sample management system could produce such a failure by improperly diluting the sample or sample and reagent combination.

Analysis of the failure of the reagent management system identified the following possible failure causes in that system: 1) false trip of a capacitance level sense (associated with reagent probe 100) due to foaming of the reagent, 2) false trip of a capacitance level sense due to fatigued lead connected to sensor, 3) defective fluidics (e.g., leakage from pump seals, fittings, tubing, sticking valves etc.), 4) drive failure of reagent probe arm (e.g., stepper motor stall), 5) plugged reagent probe (e.g., as a result of protein buildup), 6) failure to detect empty reagent pack, 7) move failure of reagent probe arm. The probability of occurrence of each such failure was deduced through observation of iterative operations of the analyzer. Possible solutions to each cause were conceptualized. These could include: a reagent algorithm verification enhancement (RAVE), anti-foaming agent added to reagents, a resilient, electrically conductive contact pad to verify function of capacitance level sensor by touching with probe between dispense cycles, and sensors to verify reagent metering transport positions. Anti-foaming agents will negatively effect performance on some assays. The contact pad and position sensors require additional hardware, address only one failure mode each (thus, have a lower overall probability of detecting system failures) and may require adding time to the metering cycle. The RAVE process also provided the most acceptable projected false positive probability.

The RAVE process is directed to rapidly washing the reagent probe 100 and determining whether sufficient fluid movement through the probe has been obtained. For example, one could correlate fluid movement through the probe with occlusion of it if the movement of fluid through the probe could be accurately verified. If sufficient fluid is moving through the probe then it can be assumed that a sufficient quantity of reagent is also aspirated and dispensed by that same probe.

In step 1 of this process, reagent probe 100 is lowered into reagent wash station 165 prior to the performance of an assay. The probe 100 is inserted into the probe wash cylinder to about one third to two-thirds of its length (typically, about 6.5 cm or 3 cm from the bottom of the wash cylinder 165). About 600 µl of wash fluid is preferably dispensed from the inside of the probe via pressurized injection into the wash station inlet port 170. Preferably, the port is about 0.25 to 0.4 cm in diameter and 1.5 cm in length. Wash fluid is injected into the probe at 482 µl/second for a probe orifice of 1.35 cm. Probe wash cylinder 165 is typically between about 9.25 and 10.75 cm long and 6.5 and 6.2 cm in diameter.

The probe wash cylinder can be fashioned from different geometries and dimensions but considerations should be given to the ability to differentiate between residual fluid retained in the wash cylinder and fluid dispensed into the cylinder during the iteration of the RAVE process being evaluated. This can become an issue if the cylinder is too wide. On the hand, if the cylinder is too narrow then fluid used to wash the probe (but not evaluate performance) may get trapped and hinder in the ability to detect a true failure. Using the conditions and equipment dimensions identified above, it was found that about 1 cm from the bottom of the cylinder where the probe stopped sensing for fluid was needed to assure a high probability that a true failure is detected. Given the step resolution of the preferred embodiment (392 steps per cm), it can be seen that a cavity that is twice the diameter of that described above would still perform acceptably but would, of course, require a greater volume of fluid dispensed. The skilled artisan will readily appreciate that an acceptable detection process requires the balancing of step resolution, wash cylinder diameter, probe travel distance and the cavity size at the bottom of the wash station, the determination of which is well within the methods known in the art. These factors all scale well. Thus one of ordinary skill can use the preferred dimensions and parameters identified herein to apply this process in other systems by scaling the factors appropriately.

In step 2 of the RAVE process, the wash fluid is evacuated through wash station exit port 160 via the application of vacuum at between 35 and 54 cm Hg. Typically, wash station exit port 160 has about the same dimensions as wash station inlet port 170.

In step 3 of the process, wash solution is forced through reagent probe 100 at about 22 psi. Preferably, about 600 µl is injected. Preferably, the probe begins dispensing at a height of about 30 mm from the bottom of the probe wash cylinder 165 and moves upward while dispensing to a height of about 40 mm from the bottom of the probe wash cylinder. Where the sensing method used to detect the presence of the foam is based on capacitance it is important to ensure that there is a transition in capacitance so that absence of foam and presence of foam are distinguishable. This is preferably accomplished by moving the probe upward during the dispense cycle in this step. In any event, the fluid is forced through the probe at a pressure sufficient to cause it to foam to a height of about 27 mm. Foam, as the term is used here, means a fairly homogeneous mixture of gas and liquid (preferably air). Such a foam has an optical density throughout that is at least about 10% different than the liquid itself. In the most preferred embodiment of this invention, the liquid is a wash solution comprising a surfactant, a potassium based buffer and minor amounts of antimicrobials.

The wash station is preferably made of a transparent polymer that can be machined such as the acrylic polymers well known in such applications. Wash solutions and wash stations made from other materials will produce different foaming characteristics which are readily determined empirically by simply forcing the wash fluid through the wash station at different pressures and characterizing the resulting foam in terms of height and capacitance in a charged field. Despite the difference in the foaming characteristics from the wash solution described here, the foams will nevertheless be capable of repeatable sensing within the quantities necessary for volumetric determinations of reagent metering. In step 4 of this process the reagent probe is lowered into the probe wash cylinder until it first makes contact with the foam produced in step 3. Preferably, the probe 100 is comprised of a conducting material such as a metal or conductive polymer so that its body can be used to detect changes in capacitance and thus serve as a level sensor as is well known in the art. It was unexpected that the probe could accurately and precisely detect the height of the foam (as opposed to that of a pure liquid). ). Yet over 6800 iterations of this process have shown this to be the case with an mean detection point of 1.31 cm from where the probe starts to sense for fluid and an imprecision of 0.19 cm (for one SD). In addition to increasing the speed of the process, accurate and precise measurements are facilitated by sensing foam and not pure liquid since this avoids fluid bridging from the bulk fluid to the interior of the probe. Thus, the probe is kept at a distance from the bulk liquid sufficient to avoid fluid bridging. This aspect of the process can also be enhanced by moving the probe upward while fluid is being dispensed from it. In the most preferred embodiment described here, in step 4 of the process the probe is lowered by a stepper motor in increments of about 392 steps per cm and 2500 steps per second. A reagent dispense failure is signaled via communication to the data processing system that no fluid has been detected to a minimum height indicative of a predetermined satisfactory quantity of reagent. Preferably, this is a height of about 10 mm from the bottom of the probe wash cylinder corresponding to a fluid volume of less than about 200 μl . The skilled artisan will readily apply the same technique to analyzers requiring dispensing of different volumes of fluid using probes, fluid flow rates, and wash stations having different characteristics and dimensions.

In step 5 of this process, vacuum is applied to the exit port 160 and the wash fluid is evacuated from the cylinder 165. Optionally, additional wash fluid is dispensed from the exterior shower as it is raised upward through the cylinder during this step. Preferably, about 200 ml of wash fluid is dispensed during this step. Preferably, about 200 ml of wash fluid is dispensed during this step. This creates no disruption or lengthening of the overall reagent metering process since vacuum is already applied during this step of the RAVE process.

The reagent algorithm verification enhancement was conducted over 6,000 iterations with the probability of observing a false error determined to be less than 3 in 1,000,000. While the RAVE solution would ultimately detect and report the effect of each of the errors listed, other solutions would at most detect the effect of some failure causes other than the targeted cause but would miss others. The RAVE solution, being targeted at the plugged probe cause (that might occur while the analyzer is running testing) produces the highest probability of detecting all related failures with a concomitantly low probability of falsely detecting an error. For example, fluidics failures such as switching valve failures (where a three way valve does not switch to a correct position) are also detected with this process despite the inherent difficulty of detecting such failures since such pumps still pump fluid. The RAVE solution has also been shown to detect partially plugged probes where a partially plugged probe fails the test because the fluid was not dispensed quickly enough. An important aspect of the reagent algorithm verification enhancement is that it can be conducted without interrupting other processes occurring in the analyzer. As a result this failure detection method can be applied without any significant decrease in throughput. It also enables a real time detection process so that the detection and identification is immediate.

Another preferred embodiment concerns the processing system. Here it was found that a failure to attain chemiluminescent signal or a signal that indicates less of an analyte than is actually present could result from metering an improper quantity of signal reagent.

Analysis of the failure to properly meter signal reagent identified the following possible failure causes: 1) signal-reagent pack failure (e.g., leaks, use of an empty pack, etc.), 2) defective fluidics (e.g., inappropriate pump movement such as too much or too little pumping), 3) fluid steer error (e.g., signal reagent delivered to a location other than a well), 4) improperly positioned well. The probability of occurrence of each such failure was deduced through observation of iterative operations of the analyzer. Possible solutions to each cause were conceptualized. These included: a dynamic in-well signal reagent verification enhancement (DIVE), in-line optical or ultrasonic bubble detector or pressure transducer to verify pump functions, ultrasonic or optical reflective sensor to measure fluid depth in reservoir, and an encoder on pump motor. Again, as in the example of RAVE, above, the technical alternatives to DIVE are either limited a single failure mode or rely on unproven technology. Accordingly, DIVE presented the highest probability of failure detection and the most acceptable probability of false positives.

Figure 5:
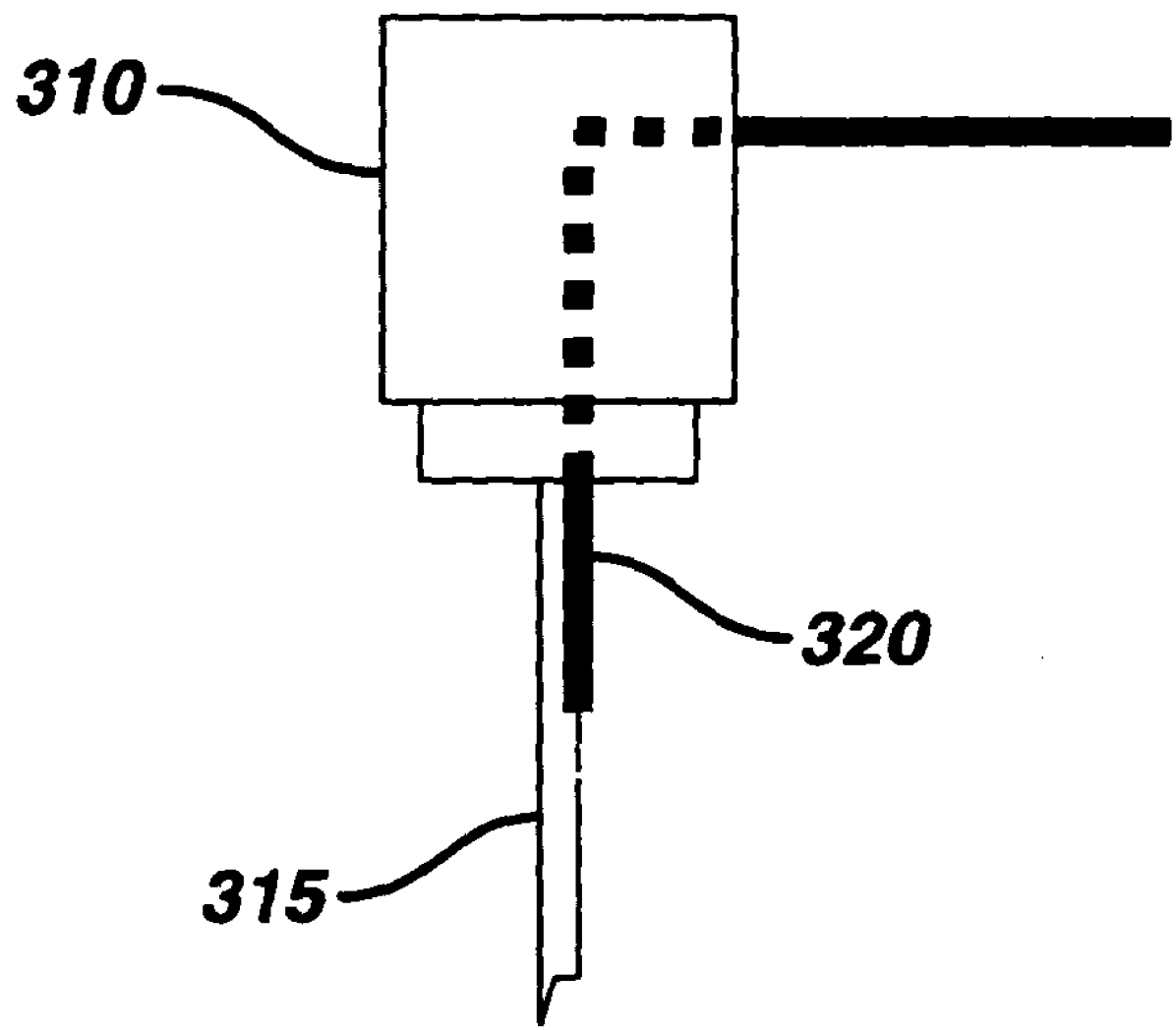
FIG. 5 is a schematic representation of a modified signal reagent probe of a clinical analyzer.

The DIVE process employs the well wash probe 315 as a level sense device to verify that sufficient signal reagent has been delivered to a well prior to reading a signal with luminometer 500. In a most preferred embodiment, well wash probe 315 is notched at its end as shown in FIG. 5. The well wash probe is preferably a conductive material such as a metal or conductive polymer so that it may function as a capacitance level sensor in a manner similar to the way that the reagent probe 100 functions as a level sensor in RAVE described above. An electrode can be affixed to the outside of the probe so that a signal can be communicated to the data processing system according to well-known methods.

Configuration of the well wash probe is dependent on accuracy and precision requirements of the analyzer as well as reaction vessel (well) geometry. In the most preferred embodiment, the accuracy, precision, and metering requirements are as described above and the well is a conical cup as described above; maximum volume is 295 to 315 μl, the base is circular with a diameter of about 4.40 mm, the open end is circular with a diameter of about 4.47 mm, and the height is about 11.41 mm More preferably, the open portion is an annular portion that extends upward from the cup from about 3.8 mm. Having such an annular extension permits linear treatment of sensing measurements within that region. That is, where the lowering of the probe/sensor into the cup is accomplished via step motor, each step correlates to the same volume measured as any other step within the linear region.

In any event, fluid height is sensed and correlated to fluid volume within the cup after signal reagent fluid has been dispensed into the well. Preferably, the well wash probe 315 is lowered via manipulation of a stepper motor with each step being counted by the data processing system 600. Vertical drive resolution of about 39 steps per mm is preferred. The process continues until the tip of well wash probe 315 contacts fluid. The height of the descent is then converted to a volumetric measurement of the total of sample, reagent, and signal reagent via a formula, or by reference to a table or data base made from a formula or derived empirically. A suitable formula is readily derived by empirically establishing the proper height, graphically depicting the descent of well wash probe until contact is made in a vessel (according to scale) using a commercial CAD software tool, and querying the CAD program to produce the equation that converts the height to volume.

Using the well wash probe 315 as a sensor in addition to its function for dispensing wash fluid to the well introduces a possibility of carryover from well to well. The extent of the carryover depends upon the diameter of probe opening, the surface tension of the fluid in the well, the depth of probe insertion upon sensing fluid, the composition of the probe and fluid, and other factors. Thus, one could ameliorate carryover by addressing some or all of these variables. The most preferred method for ameliorating all of these effects is to notch the probe end. Where the probe opening has a diameter of between about 1.347 mm and 1.397 mm is circular, and can be caused to step at increments of about 0.0254 mm, as in the case of the most preferred embodiment, a rectangular protrusion of about 0.050 mm in width at a height of about 0.76 mm is preferred. This greatly reduces the possibility of fluid bridging and hence reduces carryover to insignificant levels. Indeed, the DIVE process is considered carryover-free since less fluid than will generate is carried over from well to well (even after 30 iterations) than is necessary to generate any detectable signal.

The DIVE process was conducted over 22,000 iterations with the probability of observing a false positive error determined to be less than 1 in 4400. In another test, wells were underfilled and overfilled to represent the specified upper and lower volume detection limits for DIVE. There were no false negatives out of 900 wells.

Another preferred embodiment of the invention is a process for detecting errors where assays require a dilution. Here too, a failure can result in the absence of a detectable signal or the production of a signal that is far weaker than would be representative of analyte concentration or activity. Such an event would occur when too much diluent was added during the dilution protocol described above. Of course, it is also possible that too little diluent can be added. In such a case, a signal that is stronger than would be representative of analyte concentration would be attained. Thus, in identifying failures of the sample metering subsystem of the sample management system, an additional failure mode is addressed thereby further contributing to the mulitiplicative product of the probability of failure detection (i.e., by the probability of an error created by underdilution).

Analysis of the failure to properly dilute samples identified the following possible failure causes: 1) bubble aspiration during swish mixing 2) defective fluidics (e.g., inappropriate pump movement such as too much or too little pumping), 3) occluded sample probe or sample probe tip, 4) misdirected diluent flow stream. The probability of occurrence of each such failure was deduced through observation of iterative operations of the analyzer. Possible solutions to each cause were conceptualized. These included: a swish mixing accuracy in-well level sense (SAILS) process, capacitive, optical, ultrasonic, gravimetric, or pressure-based verification of pump functions and/or of the amount of fluid diposited into the dilution well, and an encoder on the reagent pump motor. The SAILS process offered the best overall probability of detecting failure with the most acceptable expected level of false positives.

In the SAILS process sample in a well is driven to a location reachable by the proboscis 230 as described above. Sample is metered into a dilution well as described above. The reagent probe 100 meters and dispenses diluent into the dilution well as described above. The total of sample and diluent volume is then determined using a sensor. While any sensor capable of measuring volume/liquid height could be used, the most preferred arrangement is to configure the proboscis 230 as a pressure sensor. In such a configuration, proboscis 230 is manipulated downward toward the dilution well with a stream of gas (preferably air) being blown from the tip. The proboscis is lowered in the same fashion as described above with respect to the reagent probe and signal reagent probe in the RAVE and DIVE processes. The sample pump (internal to sample metering arm 245) is fitted with a pressure transducer detects the fluid surface at fluid contact. The descent of the proboscis is then signaled to the data processing system where the volume of fluid in the well is determined in the same fashion as in the DIVE process. If too great or too little a total volume of sample and diluent are sensed, a failure is reported. Unless an error is detected the sample and diluent are swish mixed as described above. Alternatively, the process can use an extra step of aspirating a portion or all of the contents of a well containing too great a volume of liquid so that spillage and contamination are avoided.

The process can also be conducted so that reagent is metered into the dilution vessel before or after any of the other components. The volume of the sample plus diluent plus reagent could then be determined by sensing the height of the combination and relating its respective volume to the measured height. Swish mixing could then be conducted on the combination of sample, reagent, and diluent. This, however, is not the preferred method.

In each of the foregoing preferred processes, failure detection is signaled to the data processing system. The use of that signal can be manifold. The preferred use is to cancel the further performance of the assay for which a failure was identified and produce an error message indicating where the failure was detected. In most cases, one or more causes can be attributed to the failure and so can be identified on the error message delivered to the user. In some cases, the failure can be used to initiate further diagnostic (including self-diagnostic) protocols to identify and ameliorate system problems. Additionally, it is possible to use certain failure identification signals to redirect an operation. For example, where insufficient reagent quantities are sensed, an additional wash cycle can be automatically programmed so that a sample experiencing such a failure is given another opportunity for analysis.

Taking two or more of the preferred embodiments in combination, one of ordinary skill will understand how the process of selecting failure detection schemes is applied.

Table 1 below shows the cumulative system effect of a suite of detection systems that have been specifically selected to augment each other. For illustration, several failure modes of the reagent metering system were chosen for the cases of reagent delivery and of dilution to show how the various detection systems interact. As each layer of detection is added left to right the cumulative effect on false negative probability is shown. At the bottom of the far right column is the combined probability for a false negative, i.e. assay failure, for all the failure modes of the reagent metering system for each case. The bottom lines in each case show the level of effectiveness required for each detection system if each failure mode had its own detection system.

Each of the new detection systems described herein has been tested to establish its inherent precision. These precision numbers were used to analytically determine rates of false positives and false negatives and the effectiveness of the detection system. These numbers are reflected in the spreadsheet below. ALU checks are light unit measurements to determine the presence of signal reagent. These checks consider abnormally low light measurement as an indication that sufficient signal reagent is not present.

| Failure Causes: | Baseline Probability | Existing Detection Level Inventory effectiveness | False Negative Probability | Existing Detection Pump move audit effectiveness | False Negative Probability | Existing Detection Metering arm move audit effectiveness |
|---|---|---|---|---|---|---|
| Failure: No Delivery of Reagent | | | | | | |
| False trip of capacitive level sense due to foaming | 1:600,000 | 25.0% | 1:800,000 | 0.0% | 1:800,000 | 0.0% |
| False trip of capacitive level sense due to sensor lead fracture | 1:250,000 | 95.0% | 1:5,000,000 | 0.0% | 1:5,000,000 | 0.0% |
| Catastrophic failure/leakage of pump seats, tubing, fittings, etc. | 1:5,000,000 | 0.0% | 1:5,000,000 | 0.0% | 1:5,000,000 | 0.0% |
| Drive failure of pump (belt break, bearing sieze, motor stall, etc.) | 1:1,000,000 | 0.0% | 1:1,000,000 | 99.0% | 1:100,000,000 | 0.0% |
| Totally plugged reagent metering probe | 1:500,000 | 0.0% | 1:500,000 | 0.0% | 1:500,000 | 0.0% |
| Move failure of reagent metering arm | 1:500,000 | 0.0% | 1:500,000 | 0.0% | 1:500,000 | 99.0% |
| 3 way value sticks common to reservoir | 1:750,000 | 0.0% | 1:750,000 | 0.0% | 1:750,000 | 0.0% |
| Combined Probabilities | 1:81,967 | | 1:125,261 | | 1:142,993 | |
| | | Single Point Detection Method effectiveness | | | | |
| If comparable level of protection were to be achieved with a single sensor monitoring each of the failure causes: → | 1:81,967 | 96.23% | 1:2,174,197 | | | |
| Failure: No Delivery of Diluent | | | | | | |
| False trip of capacitive level sense due to foaming | 1:600,000 | 25.0% | 1:800,000 | 0.0% | 1:800,000 | 0.0% |
| False trip of capacitive level sense due to sensor lead fracture | 1:250,000 | 95.0% | 1:5,000,000 | 0.0% | 1:5,000,000 | 0.0% |
| Catastrophic failure/leakage of pump seats, tubing, fittings, etc. | 1:5,000,000 | 0.0% | 1:5,000,000 | 0.0% | 1:5,000,000 | 0.0% |
| Drive failure of pump (belt break, bearing sieze, motor stall, etc.) | 1:1,000,000 | 0.0% | 1:1,000,000 | 99.0% | 1:100,000,000 | 0.0% |
| Totally plugged reagent metering probe | 1:500,000 | 0.0% | 1:500,000 | 0.0% | 1:500,000 | 0.0% |
| Move failure of reagent metering arm | 1:500,000 | 0.0% | 1:500,000 | 0.0% | 1:500,000 | 99.0% |
| 3 way valve sticks common to reservoir | 1:750,000 | 0.0% | 1:750,000 | 0.0% | 1:750,000 | 0.0% |
| Combined Probabilities | 1:81,967 | | 1:125,261 | | 1:142,993 | |
| | | Single Point Detection Method effectiveness | | | | |
| If comparable level of protection were to be achieved with a single sensor monitoring each of the failure causes: → | 1:61,967 | 99.372% | 1:13,052,104 | | | |

| Failure Causes: | False Negative Probability | New Detection ARCH effectiveness | False Negative Probability | New Detection RAVE effectiveness | False Negative Probability | New Detection ALU effectiveness |
|---|---|---|---|---|---|---|
| Failure: No Delivery of Reagent | | | | | | |
| False trip of capacitive level sense due to foaming | 1:800,000 | 0.0% | 1:800,000 | 0.0% | 1:800,000 | 70.0% |
| False trip of capacitive level sense due to sensor lead fracture | 1:5,000,000 | 3.0% | 1:5,154,639 | 99.0% | 1:515,463,918 | 70.0% |
| Catastrophic failure/leakage of pump seats, tubing, fittings, etc. | 1:5,000,000 | 3.0% | 1:5,154,639 | 99.0% | 1:515,463,918 | 70.0% |
| Drive failure of pump (belt break, bearing sieze, motor stall, etc.) | 1:100,000,000 | 3.0% | 1:103,092,784 | 99.0% | 1:10,309,278,351 | 70.0% |
| Totally plugged reagent metering probe | 1:500,000 | 3.0% | 1:515,484 | 99.0% | 1:51,546,392 | 70.0% |
| Move failure of reagent metering arm | 1:50,000,000 | 3.0% | 1:61,548,392 | 99.0% | 1:5,154,639,175 | 70.0% |
| 3 way value sticks common to reservoir | 1:750,000 | 3.0% | 1:773,196 | 80.0% | 1:3,865,979 | 70.0% |
| Combined Probabilities | 1:199,468 | | 1:204,064 | 99.0% | 1:652,640 | |
| If comparable level of protection were to be achieved with a single sensor monitoring each of the failure causes: → | | | | | | |
| Failure: No Delivery of Diluent | | | | | | |
| False trip of capacitive level sense due to foaming | 1:800,000 | 0.0% | 1:800,000 | 0.0% | 1:800,000 | 0.0% |
| False trip of capacitive level sense due to sensor lead fracture | 1:5,000,000 | 3.0% | 1:5,154,639 | 99.0% | 1:515,463,918 | 0.0% |

-continued

| Failure Causes: | Baseline Probability | Existing Detection Level Inventory effectiveness | False Negative Probability | Existing Detection Pump move audit effectiveness | False Negative Probability | Existing Detection Metering arm move audit effectiveness |
|---|---|---|---|---|---|---|
| Catastrophic failure/leakage of pump seals, tubing, fittings, etc. | 1:5,000,000 | 3.0% | 1:5,154,639 | 99.0% | 1:515,463,918 | 0.0% |
| Drive failure of pump (belt break, bearing sieze, motor stall, etc.) | 1:100,000,000 | 3.0% | 1:103,092,784 | 99.0% | 1:10,309,278,351 | 0.0% |
| Totally plugged reagent metering probe | 1:500,000 | 3.0% | 1:515,484 | 99.0% | 1:51,546,392 | 0.0% |
| Move failure of reagent metering arm | 1:50,000,000 | 3.0% | 1:51,548,392 | 99.0% | 1:5,154,639,175 | 0.0% |
| 3 way valve sticks common to reservoir | 1:750,000 | 3.0% | 1:773,196 | 80.0% | 1:3,865,979 | 0.0% |
| Combined Probabilities | 1:199,468 | | 1:204,064 | 99.0% | 1:652,640 | |
| If comparable level of protection were to be → achieved with a single sensor monitoring each of the failure causes: | | | | | | |

We claim:

1. A method of detecting fluid metering failures comprising:
   a) rapidly flushing a fluid delivery vessel with a fluid so that a foam is formed by the fluid,
   b) measuring the height of the foam within a vessel without measuring a height of a liquid underlying the foam,
   c) evaluating the sufficiency of the volume of the fluid based on the height of the foam, and
   d) identifying insufficient volumes as fluid metering failures.

2. The method of claim 1 wherein said measuring step is conducted by a level sensor.

3. The method of claim 2 wherein said level sensor is a pressure sensing, capacitance, reflected energy, or visual detection sensor.

4. The method of claim 1 wherein the method of detecting fluid metering failures is fast enough so that it can be done without impacting system throughput.

5. The method of claim 1 wherein the method is able to detect:
   a) partially plugged reagent probes,
   b) fully plugged reagent probes, and
   c) failed valves.

6. The method of claim 1 wherein said measuring step is conducted by a capacitance sensor.

7. The method of claim 1 further comprising the step of determining the volume of the fluid.

8. A method of detecting analyzer failures comprising:
   I) a) rapidly flushing a fluid delivery vessel with a fluid so that a foam is formed by the fluid,
      b) measuring the height of the foam within a the vessel without measuring a height of a liquid underlying the foam,
      c) determining the volume of the fluid,
      d) evaluating the sufficiency of the volume of the fluid,
      e) identifying insufficient volumes as fluid metering failures, and
   II) a) aspirating sample in a fluid delivery device,
      b) metering sample into a dilution vessel,
      c) metering diluent into said dilution vessel,
      d) determining the volume of b) and c),
      e) determining the sufficiency of the measurement taken in d), and
      f) identifying as a failure insufficiencies identified in e).

9. The method of claim 8 further comprising:
   III) employing a carryover free fluid delivery and verification device comprising a hollow vessel through which fluid is dispensed having an end out of which fluid is dispensed, said vessel being in contact with a transducer, wherein said end out of which fluid is dispensed comprises a geometry resistant to carryover.

* * * * *